(12) United States Patent
Kim

(10) Patent No.: US 8,527,079 B2
(45) Date of Patent: Sep. 3, 2013

(54) ON-LINE SYSTEM FOR MANUFACTURING A DENTAL MOLD

(76) Inventor: Jin Hwan Kim, Seoul (KR)

(*) Notice: Subject to any disclaimer, the term of this patent is extended or adjusted under 35 U.S.C. 154(b) by 309 days.

(21) Appl. No.: 13/034,241

(22) Filed: Feb. 24, 2011

(65) Prior Publication Data

US 2012/0221135 A1 Aug. 30, 2012

(51) Int. Cl.
*G06F 19/00* (2011.01)
(52) U.S. Cl.
USPC .............................. 700/98; 345/420; 433/24
(58) Field of Classification Search
USPC ............................. 700/98; 345/420; 433/24
See application file for complete search history.

(56) References Cited

U.S. PATENT DOCUMENTS

| | | | |
|---|---|---|---|
| 2002/0055800 A1* | 5/2002 | Nikolskiy et al. | 700/98 |
| 2005/0064360 A1* | 3/2005 | Wen et al. | 433/24 |
| 2005/0177266 A1* | 8/2005 | Kopelman et al. | 700/117 |
| 2008/0021584 A1* | 1/2008 | Whaite et al. | 700/109 |
| 2012/0065756 A1* | 3/2012 | Rubbert et al. | 700/98 |

* cited by examiner

*Primary Examiner* — Mohammad Ali
*Assistant Examiner* — Anthony Whittington
(74) *Attorney, Agent, or Firm* — Cantor Colburn LLP

(57) ABSTRACT

An on-line system for manufacturing a dental mold is provided. In one embodiment, An on-line system for manufacturing a dental mold may comprise a user terminal configured to receive graphic data of a damaged tooth, a tooth adjacent to the damaged tooth and a tooth occluded with the damaged tooth, which are obtained by a 3D scanner, and to generate graphic data of a restoration tooth based on the received graphic data; a dental mold data management server configured to receive the graphic data of the restoration tooth from the user terminal; and one or more dental mold manufacturing apparatuses configured to receive the graphic data of the restoration tooth from the dental mold data management server and to manufacture the dental mold corresponding to the graphic data of the restoration tooth.

8 Claims, 8 Drawing Sheets

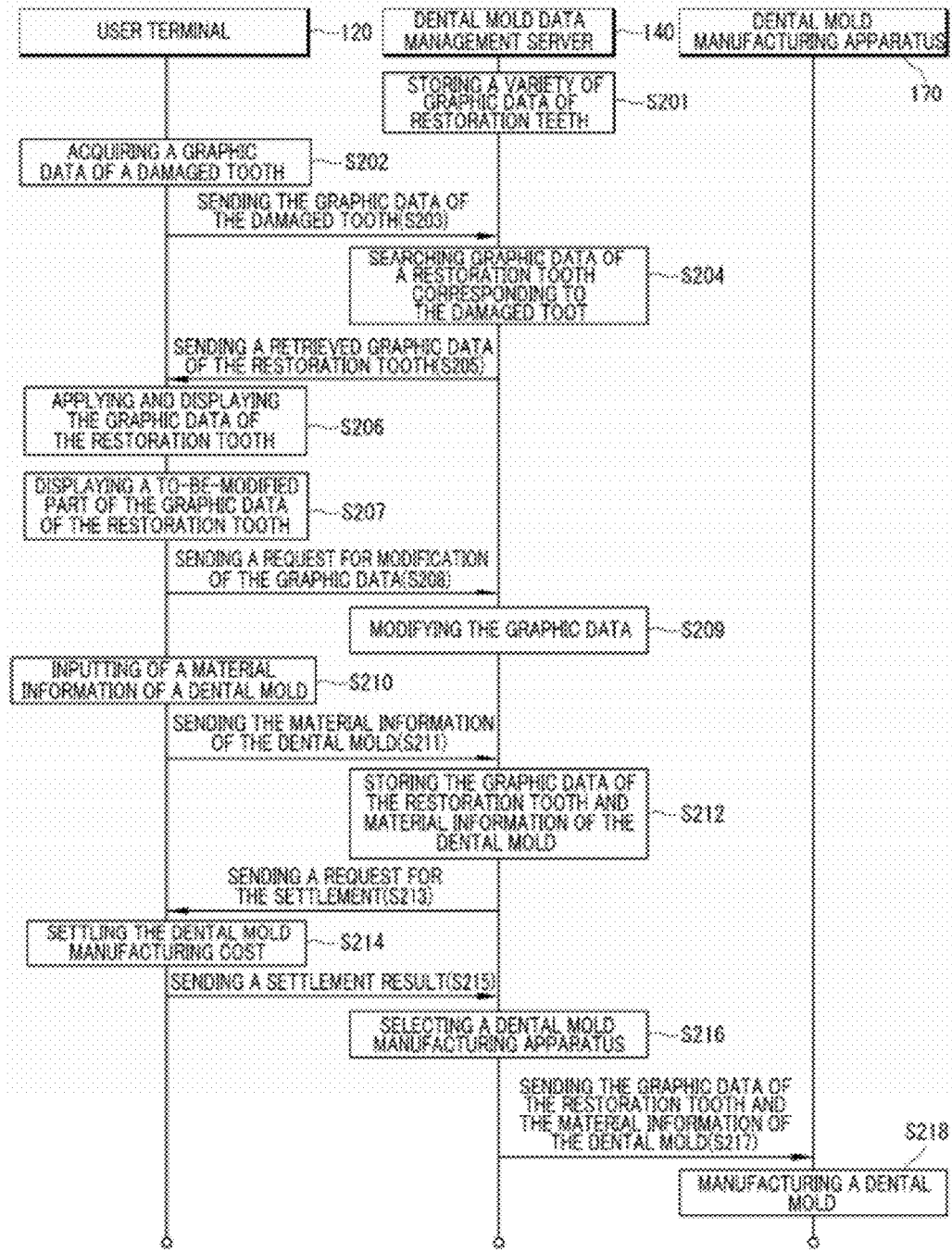

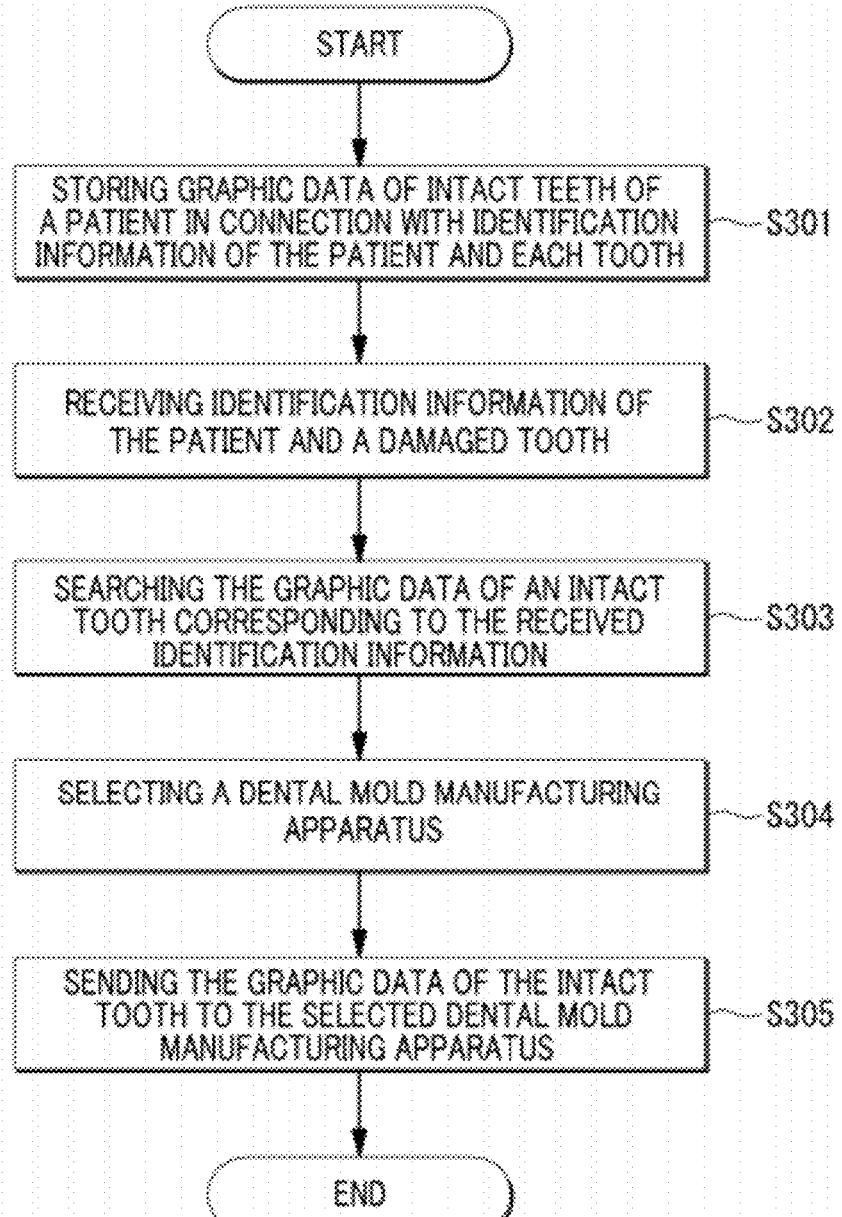

ON-LINE SYSTEM FOR MANUFACTURING A DENTAL MOLD

FIELD OF THE INVENTION

The present disclosure relates to an on-line system and method for manufacturing a dental mold by generating graphic data of a restoration tooth based on graphic data of a to-be-treated part obtained by a 3D scanner and sending the generated graphic data of the restoration tooth to one of a multiple number of dental mold manufacturing apparatuses.

BACKGROUND OF THE INVENTION

In general, a dental treatment performed in a dental clinic refers to a process of curing functional disorders (noise generation when chewing, difficulty in masticating food, problems in pronunciation, restoration of teeth, and so forth) and aesthetic disorders (a protruding chin, an inturned tooth, and so forth) that might be generated by an abnormal dental state of a patient.

Such a dental treatment includes sequential processes of fabricating a plaster cast of patient's teeth, measuring current dental state data (inclination, position, shape, etc. of the teeth), determining a treatment method for curing abnormal parts of damaged teeth and executing the treatment by using various treatment apparatuses.

Conventionally, when a dental mold for restoring patient's damaged tooth, a plaster cast of the damaged tooth was fabricated by a dentist in a dental clinic, and a dental technician was requested to fabricate a dental mold conforming to the plaster cast.

In accordance with the conventional dental mold manufacturing method, however, since treatment data has been indirectly acquired from a teeth plaster mold to diagnose and measure the current state of the patient's teeth, great time and effort have been required.

Furthermore, in accordance with the conventional dental mold manufacturing method, a single dental lab is under contract to a limited number of dental clinics and has manufactured dental molds according to orders of dentists of those dental clinics. Thus, productivity has been low.

BRIEF SUMMARY OF THE INVENTION

In view of the foregoing, the present disclosure provides an on-line system and method for manufacturing a dental mold by directly generating graphic data of a to-be-treated part through the use of a 3D scanner without manufacturing a plaster cast of teeth; and also provides a method thereof.

Further, the present disclosure also provides an on-line system and method for manufacturing a dental mold by selecting a single dental mold manufacturing apparatus among a multiple number of dental mold manufacturing apparatus based on processing amounts of the respective dental mold manufacturing apparatuses, thus capable of allowing efficient utilization of high-price dental mold manufacturing apparatuses by a multiple number of dental clinics.

Furthermore, the present disclosure also provides an on-line system and method for manufacturing a dental mold by applying graphic data of a restoration tooth to graphic data of a damaged tooth of a patient and modifying the graphic data of the restoration tooth so as to be suitable for the damaged tooth state.

In accordance with a first aspect of the present disclosure, there is provided an on-line system for manufacturing a dental mold, comprising a user terminal configured to receive graphic data of a damaged tooth, a tooth adjacent to the damaged tooth and a tooth occluded with the damaged tooth, which are obtained by a 3D scanner, and to generate graphic data of a restoration tooth based on the received graphic data; a dental mold data management server configured to receive the graphic data of the restoration tooth from the user terminal; and one or more dental mold manufacturing apparatuses configured to receive the graphic data of the restoration tooth from the dental mold data management server and to manufacture the dental mold corresponding to the graphic data of the restoration tooth. The dental mold data management server sends the graphic data of the restoration tooth to one of the dental mold manufacturing apparatuses.

In accordance with a second aspect of the present disclosure there is provided an on-line dental mold data management apparatus, comprising a graphic data management unit configured to receive, from a user terminal, graphic data of a damaged tooth, a tooth adjacent to the damaged tooth and a tooth occluded with the damaged tooth, which are obtained by a 3D scanner, and graphic data of a restoration tooth generated based on the graphic data of the damaged tooth, the adjacent tooth and the occluded tooth; a material information management unit configured to receive material information of a dental mold from the user terminal; and a dental mold manufacturing apparatus selecting unit configured to select one of a plurality of dental mold manufacturing apparatuses. The graphic data management unit sends the graphic data of the restoration tooth to the dental mold manufacturing apparatus selected by the dental mold manufacturing apparatus selecting unit. And the material information management unit sends the material information of dental mold to the selected dental mold manufacturing apparatus.

In accordance with a third aspect of the present disclosure there is provided an on-line dental mold data management apparatus, comprising a damaged tooth graphic data management unit configured to receive graphic data of a to-be-treated part of a patient including a damaged tooth from a user terminal, the graphic data being obtained from the to-be-treated part by a 3D scanner; a restoration tooth graphic data management unit configured to search a database for graphic data of a restoration tooth corresponding to the graphic data received by the damaged tooth graphic data management unit; an application result displaying unit configured to display a result of applying the retrieved graphic data of the restoration tooth to the graphic data of the to-be-treated part; an application result modifying unit configured to modify the retrieved graphic data of the restoration tooth in response to a request from the user terminal; and a dental mold manufacturing apparatus selecting unit configured to select one of a plurality of dental mold manufacturing apparatuses. The graphic data management unit sends the graphic data of the restoration tooth or the modified graphic data of the restoration tooth to the dental mold manufacturing apparatus selected by the dental mold manufacturing apparatus selecting unit.

In accordance with the present disclosure, graphic data of the to-be-treated part can be directly generated by the 3D scanner without having to manufacture a plaster cast of teeth.

Moreover, in accordance with the present disclosure, the dental mold can be manufacture by selecting one dental mold manufacturing apparatus among the multiple number of dental mold manufacturing apparatus based on processing amounts of the respective dental mold manufacturing apparatuses. Thus, high-price dental mold manufacturing apparatuses can be efficiently utilized by a multiple number of dental clinics.

Furthermore, in accordance with the present disclosure, the dental mold can be manufactured by modifying the graphic data of the restoration tooth so as to be suitable for the damaged tooth state after the graphic data of the restoration tooth is applied to the graphic data of the damaged tooth of the patient.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and are, therefore, not to be intended to limit its scope, the disclosure will be described with specificity and detail through use of the accompanying drawings, in which:

FIG. 7 provides a flowchart to describe a method for manufacturing a dental mold in accordance with another embodiment of the present disclosure; and FIG. 8 provides a flowchart to describe an on-line method for manufacturing a dental mold in accordance with still another embodiment of the present disclosure.

DETAILED DESCRIPTION OF THE INVENTION

Figure 1:
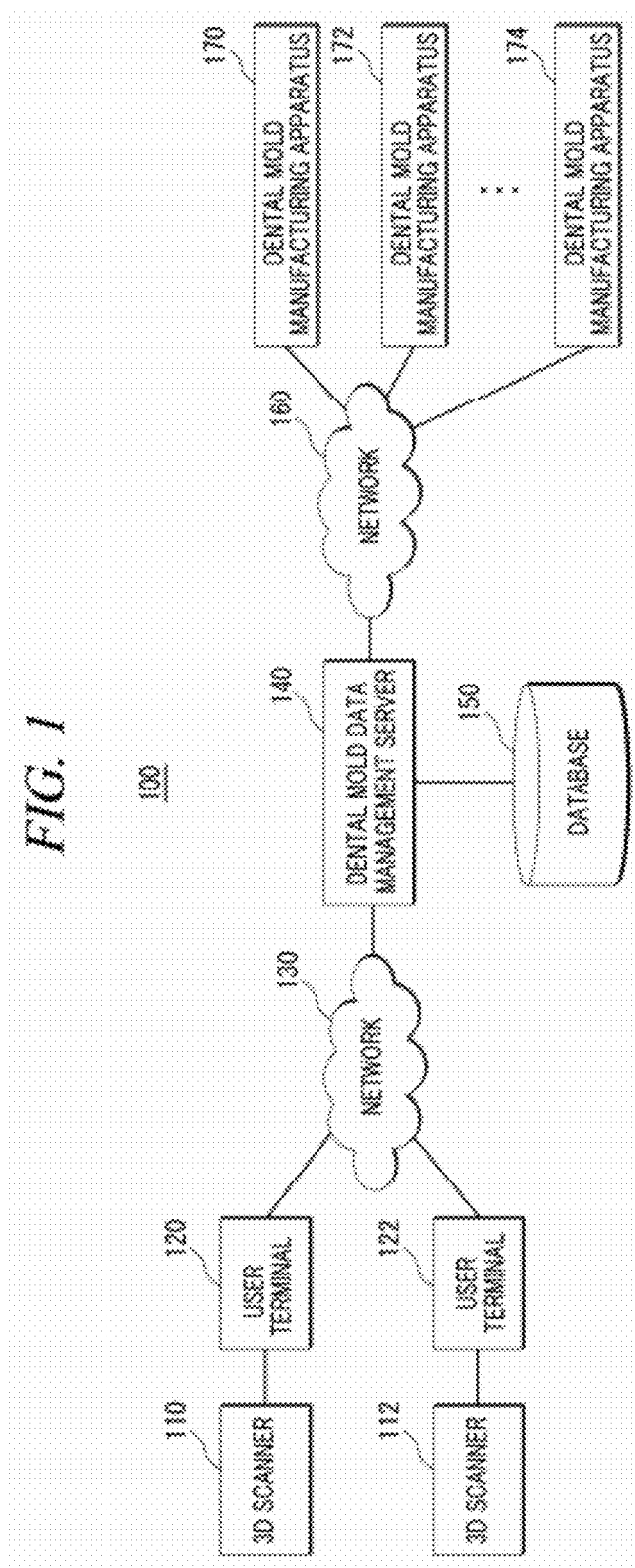
FIG. 1 is a diagram showing a relationship of linkage in an on-line system for manufacturing a dental mold in accordance with an embodiment of the present disclosure.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be realized in various other ways. In the drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, the term "comprises or includes" and/or "comprising or including" used in the document means that one or more other components, steps, operation and/or existence or addition of elements are not excluded from the described components, steps, operation and/or elements but further included unless stated otherwise.

And, the term "dental mold" used in the document may mean a dental prosthesis, a dental supplement, a dental complement, a dental implant or a dental model.

Hereinafter, an on-line system for manufacturing a dental mold and a manufacturing method thereof will be described in an embodiment of the present disclosure with reference to FIGS. 1 to 8.

FIG. 1 is a diagram showing a relationship of linkage in an on-line dental mold manufacturing system in accordance with an embodiment of the present disclosure.

Referring to FIG. 1, an on-line dental mold manufacturing system 100 in accordance with the embodiment of the present disclosure may include 3D scanners 110 and 112, user terminals 120 and 122, networks 130 and 160 and a dental mold data management server 140, a database 150 and one or more dental mold manufacturing apparatuses 170, 172 and 174.

The 3D scanners 110 and 112 scan a to-be-treated part of a patient and obtain 3D graphic data of a damaged tooth, teeth adjacent to the damaged tooth and a tooth occluded with the damaged tooth.

The user terminals 120 and 122 may be implemented by a computer such as a notebook, a desktop, a laptop installed in clinics. The user terminals 120 and 122 receive the graphic data of the damaged tooth, the teeth adjacent to the damaged tooth and the tooth occluded with the damaged tooth that are obtained by the 3D scanners 110 and 112. Then, the user terminals 120 and 122 generate graphic data of a restoration tooth based on the received graphic data. Further, the user terminals 120 and 122 receive a user input of material information designating a material (e.g., gold, resin, ceramic, zircon, or the like) to be used in the manufacture of a dental mold, and sends the received material information to the dental mold data management server 140.

Installed in the user terminals 120 and 122 is a program capable of displaying, modifying and processing the 3D graphic data of the to-be-treated part acquired by the 3D scanners 110 and 112. The program may be connected with the dental mold data management server 140 through the network 130 and sends the graphic data of the restoration tooth and the material information of the dental mold to the dental mold data management server 140. At this time, when the graphic data of the restoration tooth and the material information of the dental mold are sent, the user terminals 120 and 122 may also send patient identification information, user terminal identification information, and so forth.

Figure 2A:
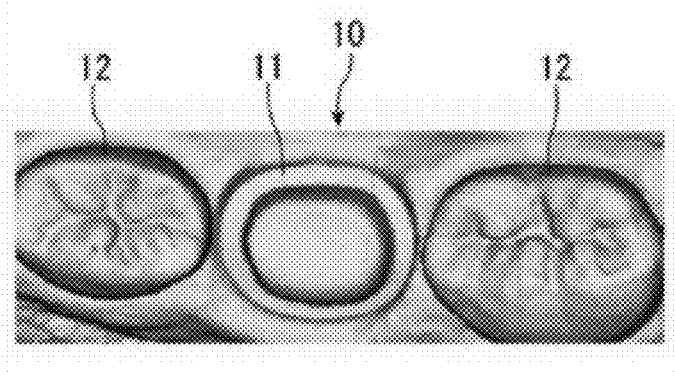
FIGS. 2A and 2B illustrate an example graphic data of a to-be-treated part in accordance with the embodiment of the present disclosure.
Figure 2B:
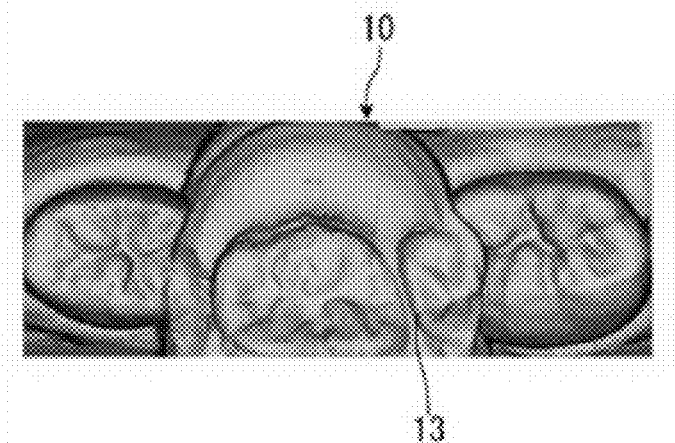
Figure 3:
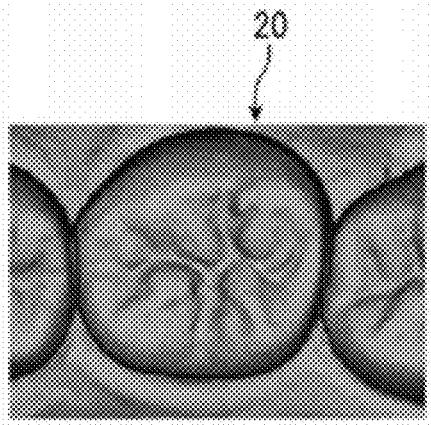
FIG. 3 illustrates example graphic data of a restoration tooth in accordance with the embodiment of the present disclosure.

FIGS. 2A and 2B illustrate an example graphic data 10 of a to-be-treated part obtained by the 3D scanners 110 and 112. FIG. 3 illustrates an example graphic data 20 of a restoration tooth generated from the graphic data 10 of the to-be-treated part.

As shown in FIG. 2A, the graphic data 10 of the to-be-treated part acquired by the 3D scanners 110 and 112 may include a damaged tooth 11 to be treated and left and right teeth 12 adjacent to the damaged tooth 11. Besides, as illustrated in FIG. 2B, the graphic data 10 of the to-be-treated part may also include graphic data of a tooth 13 occluded with the damaged tooth. The user terminal 120 may generate graphic data 20 of the restoration tooth corresponding to the damaged tooth 11 from the graphic data 10 of the to-be-treated part, as illustrated in FIG. 3.

As stated above, in accordance with the present disclosure, by acquiring the graphic data of the adjacent teeth 12 and the occluded tooth 13 as well as the damaged tooth 11, alignment of the damaged tooth 11 to its adjacent teeth, i.e., left and right adjacent teeth 12 and the occluded tooth 13 can be examined.

For reference, a treatment method for the damaged tooth 11, i.e., a restoration type of the restoration tooth may be determined depending on the state of the to-be-treated part. Such a restoration type of the restoration tooth may include inlay, onlay, partial crown, veneer, crown, and so forth.

Inlay, onlay and partial crown are methods for removing a damaged part of the damaged tooth 11 and filling the damaged part with a dental mold material, e.g., gold, resin, ceramic or zircon, or the like. Further, veneer is a method for bonding a dental mold to a front surface of the damaged tooth 11. Bridge is used when the damaged tooth 11 is extracted and it is a method for connecting adjacent healthy teeth located at the left and right side of the missing tooth. Further, crown is a method for completely capping or encircling the damaged tooth 11.

Referring back to FIG. 1, the dental mold data management server 140 is connected with the user terminals 120 and 122 through the network 130 and receives the graphic data of the restoration tooth and the material information of the dental mold from the user terminals 120 and 122. Further, the dental mold data management server 140 are also connected with the dental mold data management apparatuses 170, 172 and 174 through the network 160 and sends the graphic data of the restoration tooth and the material information of the dental mold to one of the dental mold manufacturing apparatuses 170, 172 and 174 so that the dental mold corresponding to the graphic data of the restoration tooth may be fabricated. At this time, the dental mold data management server 140 may select one of the dental mold manufacturing apparatuses 170, 172 and 174 depending on processing amounts of the respective dental mold manufacturing apparatuses.

Furthermore, the dental mold data management server 140 stores the graphic data of the restoration tooth in the database 150 in connection with the user terminal identification information, the patient identification information and identification information of the selected dental mold manufacturing apparatus.

The database 150 stores therein the graphic data of the restoration tooth received from the user terminals 120 and 122 via the dental mold data management server 140 in connection with the user terminal identification information, the patient identification information and identification information of the selected dental mold manufacturing apparatus.

Each of the networks 130 and 160 may be a wired network such as a local area network (LAN), a wide area network (WAN) or a value added network (VAN), or may be any of various kinds of wireless networks such as a mobile radio communication network, a satellite communication network, a Bluetooth, a wireless broadband internet (Wibro), a high speed downlink packet access (HSDPA), and the like.

The multiple number of dental mold manufacturing apparatuses 170, 172 and 174 are connected with the dental mold data management server 140 through the network 160, and receive the graphic data of the restoration tooth from the dental mold data management server 140 and manufacture a dental mold corresponding to the graphic data of the restoration data and the material information of the dental mold.

Figure 4:
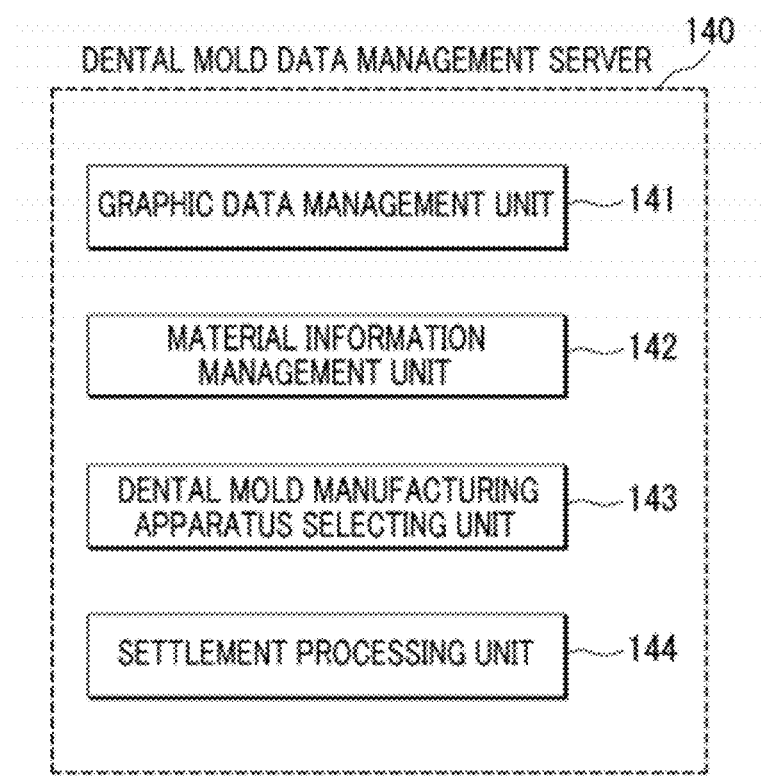
FIG. 4 is a detailed block diagram of a dental mold data management server in accordance with the embodiment of the present disclosure.

FIG. 4 is a detailed block diagram of the dental mold data management server in accordance with the embodiment of the present disclosure.

As depicted in FIG. 4, the dental mold data management server 140 in accordance with the embodiment of the present disclosure may include a graphic data management unit 141, material information management unit 142, a dental mold manufacturing apparatus selecting unit 143 and a settlement processing unit 144.

The graphic data management unit 141 receives from the user terminal 120 the graphic data of the restoration tooth generated from the graphic data of the damaged tooth, the teeth adjacent to the damaged tooth and the tooth occluded with the damaged tooth. Then, the graphic data management unit 141 stores the received graphic data restoration tooth in the database 150.

The material information management unit 142 receives from the user terminal the information of the material (e.g., gold, resin, ceramic, zircon, or the like) to be used in the manufacture of the dental mold which is to be manufactured according to the graphic data of the restoration tooth. Then, the material information management unit 142 stores the received material information in the database 150.

The dental mold manufacturing apparatus selecting unit 143 selects one of the dental mold manufacturing apparatuses 170, 172 and 174 depending on the processing amounts of the respective apparatuses. By way of example, when a request for manufacturing a dental mold is received, the dental mold manufacturing apparatus selecting unit 143 selects a dental mold manufacturing apparatus of which current processing amount is lowest.

If one dental mold manufacturing apparatus for manufacturing the dental mold corresponding to the graphic data of the restoration tooth is selected by the dental mold manufacturing apparatus selecting unit 143, the graphic data management unit 141 sends the graphic data of the restoration tooth to the selected dental mold manufacturing apparatus. Further, the material information management unit 142 sends the material information of the dental mold, to the selected dental mold manufacturing apparatus, e.g., to the first dental mold manufacturing apparatus 170.

The settlement processing unit 144 sends a request for settlement of dental mold manufacturing cost and receives a settlement result from the user terminal 120. Then, the settlement processing unit 144 tranceives settlement information from/to a server (not shown) of a card company and a server (not shown) of a financial company.

Figure 5:
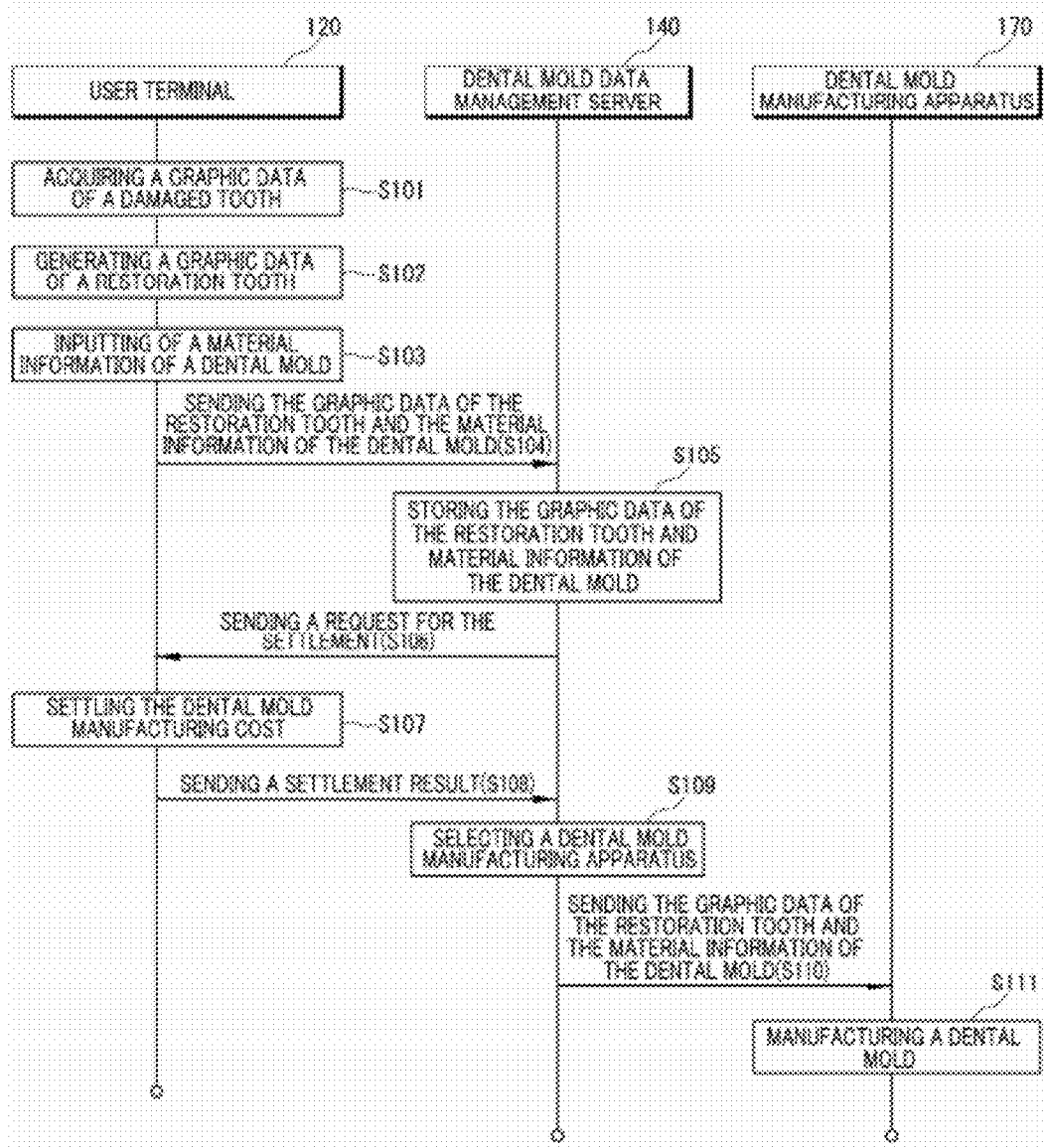
FIG. 5 provides a flowchart to describe an on-line method for manufacturing a dental mold in accordance with the embodiment of the present disclosure.

FIG. 5 provides a flowchart to describe an on-line dental mold manufacturing method in accordance with the embodiment of the present disclosure.

In step S101, the user terminal 120 acquires the graphic data of the damaged tooth, the teeth adjacent to the damaged tooth and the tooth occluded with the damaged tooth that from the to-be-treated part by using the 3D scanners 110 and 112. Then, in step S102, the user terminal 120 generates the graphic data of the restoration tooth based on the graphic data of the damage tooth, the adjacent teeth and the occluded tooth.

In step S103, the user terminal 120 receives a user input of the material information of the dental mold which is to be manufactured according to the graphic data of the restoration tooth. Then, in step S104, the user terminal 120 sends the graphic data of the restoration tooth and the material information of the dental mold to the dental mold data management server 140.

In step S105, the dental mold data management server 140 stores the received graphic data of the restoration tooth and material information of the dental mold in the database 150 in connection with the patient identification information for identifying the patient. Then, in step S106, the dental mold data management server 140 sends a request for the settlement of the manufacturing cost of the dental mold to the user terminal 120.

In step S107, the user terminal 120 settles the dental mold manufacturing cost as requested by the dental mold data management server 140. Then, in step S108, the user terminal 120 sends a settlement result to the dental mold data management server 140.

If the settlement result of the dental mold manufacturing cost is received from the user terminal 120, the dental mold data management server 140 selects one of the plurality of dental mold manufacturing apparatuses 170, 172 and 174, e.g., the first dental mold manufacturing apparatus 170 in step S109. Then, in step S110, the dental mold data management server 140 sends the graphic data of the restoration tooth and the material information of the dental mold stored in the database 150 to the first dental mold manufacturing apparatus 170 selected in the step S109. At this time, the dental mold data management server 140 selects one dental mold manufacturing apparatus depending on the processing amounts of the respective dental mold manufacturing apparatuses and stores identification information of the selected dental mold manufacturing apparatus in the database 150 in connection with the patient identification information and the user terminal identification information previously stored in the step S105.

Subsequently, in step S111, the first dental mold manufacturing apparatus 170 manufactures a dental mold according to the material information and the graphic data of the restoration tooth received from the dental mold data management server 140.

As stated above, in accordance with the on-line dental mold manufacturing system in accordance with the embodiment of the present disclosure, one of the multiple number of dental mold manufacturing apparatuses is selected based on their processing amounts, and the dental mold is manufactured by the selected manufacturing apparatus. Thus, high-prices dental mold manufacturing apparatuses can be efficiently used by a multiple number of dental clinics.

In the above description, the description has been provided for the case that the user terminal generates the graphic data of the restoration tooth from the graphic data of the to-be-treated part obtained by the 3D scanner and sends the generated graphic data of the restoration tooth to the dental mold data management server, thus allowing the dental mold to be manufactured based on the generated graphic data of the restoration tooth. However, the present disclosure may not be limited thereto. By way of example, the dental mold data management server 140 may search the database 150 for the graphic data of the restoration tooth corresponding to the graphic data of the to-be-treated part provided from the user terminal 120 and may retrieve the desired graphic data from the graphic data of a multiple number of restoration teeth previously stored in the database 150 and send the retrieved graphic data of the restoration tooth to the user terminal.

Hereinafter, a dental mold data management server configured to search a database for graphic data of a restoration tooth corresponding to a to-be-treated part to manufacture a dental mold and a method thereof will be explained.

Figure 6:
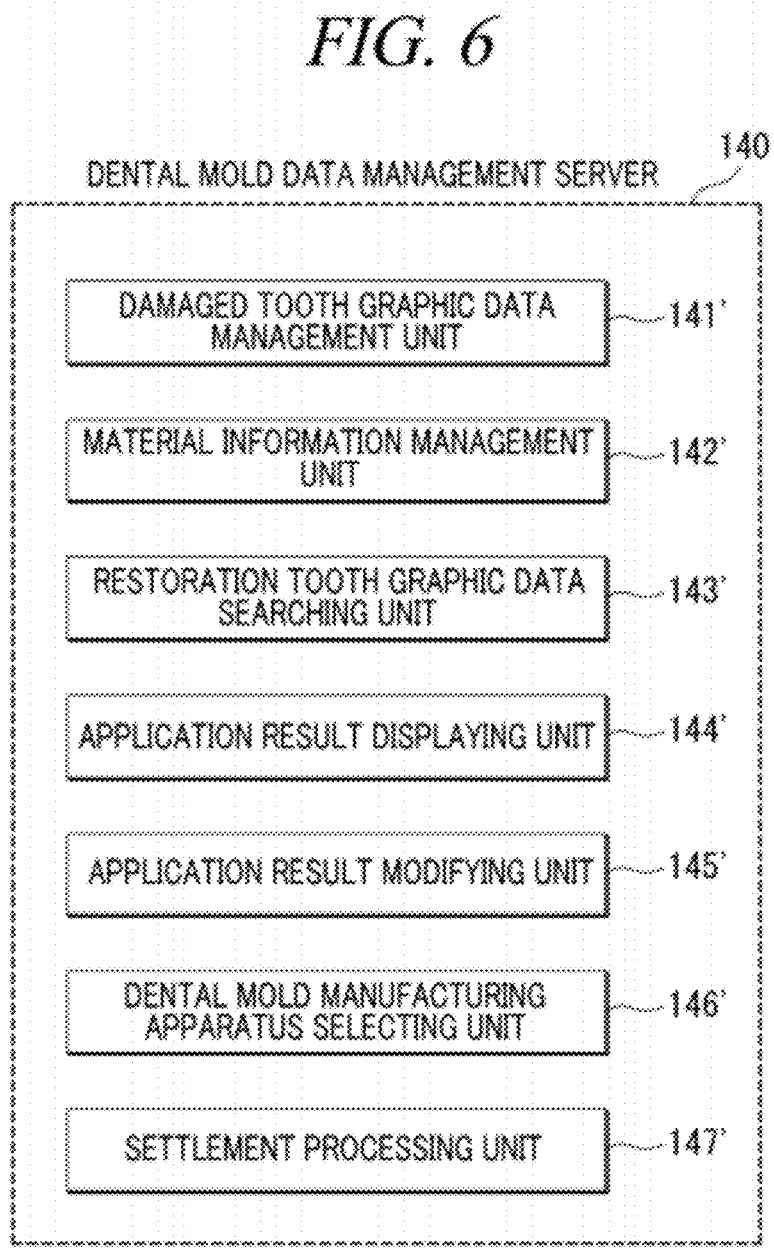
FIG. 6 is a detailed block diagram of a dental mold data management server in accordance with another embodiment of the present disclosure.

FIG. 6 is a detailed block diagram illustrating a dental mold data management server in accordance with another embodiment of the present disclosure.

As shown in FIG. 6, the dental mold data management server 140 may include a damaged tooth graphic data management unit 141', a material information management unit 142', a restoration tooth graphic data searching unit 143', an application result displaying unit 144', an application result modifying unit 145', a dental mold manufacturing apparatus selecting unit 146' and a settlement processing unit 147'.

The damaged tooth graphic data management unit 141' receives from a user terminal 120 graphic data of a to-be-treated part, i.e., graphic data of a damaged tooth, left and right adjacent teeth and a tooth occluded with the damaged tooth that are obtained by a 3D scanner 110.

The material information management unit 142' receives information of a material to be used in the manufacture of a dental mold from the user terminal 120.

The restoration tooth graphic data searching unit 143' searches a database 150 for graphic data of a restoration tooth corresponding to the graphic data of the damaged tooth that is received by the damaged graphic data management unit 141.

The application result displaying unit 144' displays on the user terminal 120 a result of applying the graphic data of the restoration tooth retrieved by the restoration tooth graphic data searching unit 143' to the graphic data of the to-be-treated part.

The application result modifying unit 145' modifies the graphic data of the restoration tooth so as to be suitable for the graphic data of the damaged tooth in response to a request from the user terminal 120.

The dental mold manufacturing apparatus selecting unit 146' selects one of a multiple number of dental mold manufacturing apparatuses 170, 172 and 174 depending on processing amounts of the respective manufacturing apparatuses. At this time, if one dental mold manufacturing apparatus is selected by the dental mold manufacturing apparatus selecting unit 146', the damaged tooth graphic data management unit 141' sends the graphic data of the restoration tooth or the modified graphic data of the restoration tooth to the selected dental mold manufacturing apparatus.

The settlement processing unit 147' sends a request for settlement of dental mold manufacturing cost and receives a settlement result from the user terminal 120. Then, the settlement processing unit 144 tranceives settlement information from/to a server (not shown) of a card company and a server (not shown) of a financial company.

FIG. 7 provides a flowchart to describe an on-line dental mold manufacturing method in accordance with another embodiment of the present disclosure.

In step S201, the dental mold data management server 140 stores a variety of graphic data of restoration teeth in the database 150.

In step S202, the user terminal 120 acquires graphic data of a damaged tooth, teeth adjacent to the damaged tooth and tooth occluded with the damaged tooth by using the 3D scanner 110. Then, in step S203, the user terminal 120 sends the graphic data of the to-be-treated part to the dental mold data management server 140.

Subsequently, in step S204, the dental mold data management server 140 searches the database 150 for graphic data of a restoration tooth corresponding to the damaged tooth based on the graphic data of the to-be-treated part received from the user terminal 120. Then, in step S205, the dental mold data management server 140 sends the retrieved graphic data of the restoration tooth to the user terminal 120.

In step S206, the user terminal 120 applies the graphic data of the restoration tooth received from the dental mold data management server 140 to the graphic data of the to-be-treated part and displays the result on a screen. Then, in step S207, the user terminal 120 displays a to-be-modified part of the graphic data of the restoration tooth applied to the graphic data of the to-be-treated part, thereby allowing the user to be visually informed.

In step S208, the user terminal 120 sends a request for modification of the graphic data of the restoration tooth to the dental mold data management server 140, and in step S209, the dental mold data management server 140 modifies the graphic data of the restoration tooth according to the request of the user terminal 120.

In step S210, the user terminal 120 receives a user input of information of a material to be used in the manufacture of a dental mold. Then, in step S211, the user terminal 120 sends the dental mold material information to the dental mold data management server 140.

In step S212, the dental mold data management server 140 stores the graphic data of the restoration tooth modified in the step S209 and the dental mold material information received in the step S211 in the database 150 in connection with patient identification information for identifying a patient. Then, in step S213, the dental mold data management server 140 sends a request for settlement of dental mold manufacturing cost.

In step S214, the user terminal 120 settles the dental mold manufacturing cost as requested by the dental mold data management server 140. Then, in step S215, the user terminal 120 sends a settlement result to the dental mold data management server 140.

If the settlement result of the dental mold manufacturing cost is received from the user terminal 120, the dental mold data management server 140 selects one of a multiple number of dental mold manufacturing apparatuses 170, 172 and 174, e.g., the first dental mold manufacturing apparatus 170 in step S216. Then, in step S217, the dental mold data management server 140 sends the graphic data of the restoration tooth and the dental mold material information stored in the database 150 to the first dental mold manufacturing apparatus 170 selected in the step S216.

Subsequently, in step S117, the first dental mold manufacturing apparatus 170 manufactures a dental mold according to the material information and the graphic data of the restoration tooth received from the dental mold data management server 140.

As stated above, in accordance with the on-line dental mold manufacturing system in accordance with the embodiment of the present disclosure, one of the plurality of dental mold manufacturing apparatuses is selected based on their processing amounts and the dental mold is manufactured by the selected manufacturing apparatus. Thus, high-prices dental mold manufacturing apparatuses can be efficiently used by a multiple number of dental clinics.

In the above description, the description has been provided for the case of manufacturing the dental mold by generating the graphic data of the restoration tooth from the graphic data of the to-be-treated part. However, the present disclosure may not be limited thereto. By way of example, it may be possible to previously capture and store images of intact teeth of a patient when the patient is not sick and manufacture a dental mold by using the graphic image of the intact teeth when a damage of a tooth occurs later.

Below, a method for manufacturing a dental mold by using graphic data of intact teeth will be explained with reference to FIG. 8.

FIG. 8 presents a flowchart to describe a method for manufacturing a dental mold in accordance with another embodiment of the present disclosure.

In step S301, a dental mold data management server 140 stores graphic data of intact teeth of a patient, which is obtained by a 3D scanner 110, in a database 150 in connection with identification information of the patient and each tooth.

In step S302, the dental mold data management server 140 receives identification information of the patient and a damaged tooth from the user terminal 120, and in step S303, the dental mold data management server 140 searches the database 150 for the graphic data of an intact tooth corresponding to the received identification information.

In step S304, the dental mold data management server 140 selects one of a multiple number of dental mold manufacturing apparatuses 170, 172 and 174, e.g., a first dental mold manufacturing apparatus 170. Then, in step S305, the dental mold data management server 140 sends the graphic data of the intact tooth retrieved in the step S303 to the first dental mold manufacturing apparatus 170 selected in the step S304.

The embodiments of the present disclosure can be embodied in a storage medium including instruction codes executable by a computer such as a program module executed by the computer. A computer readable medium can be any usable medium which can be accessed by the computer and includes all volatile/non-volatile and removable/non-removable media. Further, the computer readable medium may include all computer storage and communication media. The computer storage medium includes all volatile/non-volatile and removable/non-removable media embodied by a certain method or technology for storing information such as computer readable instruction code, a data structure, a program module or other data. The communication medium typically includes the computer readable instruction code, the data structure, the program module, or other data of a modulated data signal such as a carrier wave, or other transmission mechanism, and includes a certain information transmission medium.

The above description of the present invention is provided for the purpose of illustration, and it would be understood by those skilled in the art that various changes and modifications may be made without changing technical conception and essential features of the present invention. Thus, it is clear that the above-described embodiments are illustrative in all aspects and do not limit the present invention. For example, each component described as a single element may be implemented in a distributed manner, and components described as distributed elements may be implemented by being combined with each other.

The scope of the present invention is defined by the following claims rather than by the detailed description of the embodiment. It shall be understood that all modifications and embodiments conceived from the meaning and scope of the claims and their equivalents are included in the scope of the present invention.

While various aspects and embodiments have been described herein, other aspects and embodiments will be apparent to those skilled in the art. The various aspects and embodiments disclosed herein are for the purposes of illustration and are not intended to be limiting. Therefore, the true scope of the disclosure is indicated by the appended claims rather than by the foregoing description, and it shall be understood that all modifications and embodiments conceived from the meaning and scope of the claims and their equivalents are included in the scope of the disclosure.

What is claimed is:

1. An on-line system for manufacturing a dental mold, comprising:

a user terminal configured to receive graphic data of a damaged tooth, a tooth adjacent to the damaged tooth and a tooth occluded with the damaged tooth, which are obtained from a to-be-treated part of a patient directly by a 3D scanner, and to generate graphic data of a restoration tooth based on the received graphic data;

a dental mold data management server configured to receive the graphic data of the restoration tooth from the user terminal and to select one of a plurality of dental mold manufacturing apparatuses depending on processing amounts of the respective dental mold manufacturing apparatuses; and one or more dental mold manufacturing apparatuses configured to receive the graphic data of the restoration tooth from the dental mold data management server and to manufacture the dental mold corresponding to the graphic data of the restoration tooth, wherein the dental mold data management server selects a dental mold manufacturing apparatus having the lowest processing amount and sends the graphic data of the restoration tooth to the selected dental mold manufacturing apparatus.

2. The one-line system of claim 1, wherein the user terminal sends material information of the dental mold to the dental mold data management server, the dental mold data management server sends the material information received from the user terminal to the dental mold manufacturing apparatus, and the dental mold manufacturing apparatus selects a dental mold material corresponding to the material information and manufactures the dental mold.

3. The on-line system of claim 1, wherein the dental mold data management server stores the graphic data of the restoration tooth in a database in connection with identification information of the user terminal, identification information of the patient and identification information of the dental mold manufacturing apparatus.

4. An on-line dental mold data management apparatus, comprising:

a graphic data management unit configured to receive, from a user terminal, graphic data of a damaged tooth, a tooth adjacent to the damaged tooth and a tooth occluded with the damaged tooth, which are obtained from a to-be-treated part of a patient directly by a 3D scanner, and graphic data of a restoration tooth generated based on the graphic data of the damaged tooth, the adjacent tooth and the occluded tooth;

a material information management unit configured to receive material information of a dental mold from the user terminal; and a dental mold manufacturing apparatus selecting unit configured to select one of a plurality of dental mold manufacturing apparatuses depending on processing amounts of the respective dental mold manufacturing apparatuses, wherein the dental mold manufacturing apparatus selecting unit selects a dental mold manufacturing apparatus having the lowest processing amount, the graphic data management unit sends the graphic data of the restoration tooth to the dental mold manufacturing apparatus selected by the dental mold manufacturing apparatus selecting unit, and the material information management unit sends the material information of dental mold to the selected dental mold manufacturing apparatus.

5. The on-line dental mold data management apparatus of claim 4, further comprising:

a database configured to store therein the graphic data of the restoration tooth in connection with identification information of the user terminal, identification information of the patient and identification information of the dental mold manufacturing apparatus.

6. An on-line dental mold data management apparatus, comprising:

a damaged tooth graphic data management unit configured to receive graphic data of a to-be-treated part of a patient including a damaged tooth from a user terminal, the graphic data being obtained from the to-be-treated part directly by a 3D scanner;

a restoration tooth graphic data management unit configured to search a database for graphic data of a restoration tooth corresponding to the graphic data received by the damaged tooth graphic data management unit;

an application result displaying unit configured to display a result of applying the retrieved graphic data of the restoration tooth to the graphic data of the to-be-treated part;

an application result modifying unit configured to modify the retrieved graphic data of the restoration tooth in response to a request from the user terminal; and a dental mold manufacturing apparatus selecting unit configured to select one of a plurality of dental mold manufacturing apparatuses depending on processing amounts of the respective dental mold manufacturing apparatuses, wherein the dental mold manufacturing apparatus selecting unit selects a dental mold manufacturing apparatus having the lowest processing amount, and the graphic data management unit sends the graphic data of the restoration tooth or the modified graphic data of the restoration tooth to the dental mold manufacturing apparatus selected by the dental mold manufacturing apparatus selecting unit.

7. The on-line dental mold data management apparatus of claim 6, further comprising:

a material information management unit configured to receive material information of a dental mold from the user terminal, wherein the material information management unit sends the material information of the dental mold to the selected dental mold manufacturing apparatus.

8. The on-line dental mold data management apparatus of claim 6 further comprising:

the database configured to store therein the graphic data of the restoration tooth in connection with identification information of the user terminal, identification information of the patient and identification information of the dental mold manufacturing apparatus.

* * * * *